(12) United States Patent
Tenney et al.

(10) Patent No.: US 7,666,179 B2
(45) Date of Patent: Feb. 23, 2010

(54) MEDICAL DEVICES HAVING POROUS REGIONS FOR CONTROLLED THERAPEUTIC AGENT EXPOSURE OR DELIVERY

(75) Inventors: Barron Tenney, Haverhill, MA (US); Michael N. Helmus, Worcester, MA (US); Yixin Xu, Newton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 11/545,439

(22) Filed: Oct. 10, 2006

(65) Prior Publication Data

US 2008/0086113 A1 Apr. 10, 2008

(51) Int. Cl.
*A61K 9/22* (2006.01)
(52) U.S. Cl. ............... 604/890.1; 604/891.1; 604/19
(58) Field of Classification Search ......... 604/890.1, 604/891.1, 892.1, 19, 20
See application file for complete search history.

(56) References Cited

U.S. PATENT DOCUMENTS

| 5,128,197 | A | 7/1992 | Kobayashi et al. | 428/225 |
|---|---|---|---|---|
| 5,733,925 | A | 3/1998 | Kunz et al. | 514/449 |
| 6,314,317 | B1 * | 11/2001 | Willis | 604/20 |
| 6,540,849 | B2 | 4/2003 | DiCarlo et al. | 148/402 |
| 7,108,685 | B2 * | 9/2006 | Helmus | 604/891.1 |
| 2002/0099359 | A1 * | 7/2002 | Santini et al. | 604/521 |
| 2003/0109824 | A1 | 6/2003 | Anderson et al. | |
| 2003/0210997 | A1 | 11/2003 | Lopez et al. | |
| 2004/0193262 | A1 * | 9/2004 | Shadduck | 623/4.1 |
| 2005/0013988 | A1 | 1/2005 | Fu et al. | |
| 2006/0127442 | A1 | 6/2006 | Helmus | 424/423 |
| 2006/0129215 | A1 * | 6/2006 | Helmus et al. | 607/115 |
| 2006/0207495 | A1 | 9/2006 | Petrakis | |
| 2007/0148251 | A1 * | 6/2007 | Hossainy et al. | 424/489 |
| 2007/0224235 | A1 | 9/2007 | Tenney et al. | 424/423 |

OTHER PUBLICATIONS

Tejal A. Desai, Derek Hansford and Mauro Ferrari, "Characterization of micromachined silicon membranes for immunoisolation and bioseparation applications," J. Membrane Science, 159 (199) 221-231.

M. Haidopoulos, Doctoral Thesis, 2005-2, "Appendice B. Shape Memory Metals" 13pp. downloaded from http://www.theses.ulaval.ca/2005/22413/apc.html.

A. Lendlein, "Shape Memory Polymers—Biodegradable Sutures," Abstracted from Materials World vol. 10 No. 7, pp. 29-30 Jul. 2002., 4 pages.

(Continued)

*Primary Examiner*—Kevin C Sirmons
*Assistant Examiner*—Bhisma Mehta
(74) *Attorney, Agent, or Firm*—Mary & Williams PC; David B. Bonham

(57) ABSTRACT

According to an aspect of the invention, implantable or insertable medical devices are provided which contain the following: (a) one or more porous regions comprising pores and (b) one or more therapeutic agents which are (i) contained within the porous region, (ii) disposed beneath the porous region, or (iii) both. Moreover, the porous regions are capable of undergoing a change in configuration, such that the pores undergo a change in configuration, upon subjecting the porous regions to activating stimuli.

34 Claims, 5 Drawing Sheets

OTHER PUBLICATIONS

A Lendlein et al., "Light-Induced shape-memory polymers," *Nature*, vol. 434 Apr. 14, 2005, 879-882.

Jorma Ryhane, *Biocompatibility evaluation of nickel-titanium shape memory metal alloy*, Chapter 2. Review of the literature, 10pp. downloaded from http://herkules.oulu.fi/isbn95142217/htmlx317.html on May 31, 2006.

E.E.L Swan, K.C. Popat, C.A. Grimes, T. A. Desai, "Fabrication and evaluation of nanoporous alumina membranes for osteoblast culture," *Journal of Biomedical Materials Research Part A*, vol. 72A, Issue 3, pp. 288-295, Published Online: Jan. 14, 2005.

"Biodegradable Shape-Memory Polymer Developed," *European Medical Device Manufacturer*, Sep. 2002, 1 Page.

J. Karow, "Brushing Your Teeth May Be Good for Your Ticker," *Scientific American*, May 2001- 20-21.

A. Lendlein and S. Kelch, "Shape Memory Polymers" *Angwe. Chem Int. Ed.*, 2002, 41, 2034-2057 and the references cited therein.

See P.A. Toensmeier, "Shape memory Polymers Reshape Product Design," *Plastics Engineering*, Mar. 2005, 10-11.

N. Shevochenko et al. "Porous surface of NiTi alloy produced by plasma ion implantation," E-MRS 2005 Spring Meeting, May 31-Jun. 3, 2005, Strasbourg, France, 1 Page.

S. Nemat—Nasser et al., "Experimental characterization and micromechanical modeling of superelastic response of porous NiTi shape—memory alloy," *Journal of the Mechanic and Physics of Solids*, 53 (2005) 2320-2346.

"Calo-MER™ Shape -Memory Thermoplastics," downloaded from http://www.polymertech.com/materials/calomer.html on Apr. 4, 2006, 4 Pages.

"Actipore™ Material Introduction" downloaded from http://wwww.biorthex.com on Apr. 4, 2006, 1 Page.

* cited by examiner

US 7,666,179 B2

MEDICAL DEVICES HAVING POROUS REGIONS FOR CONTROLLED THERAPEUTIC AGENT EXPOSURE OR DELIVERY

TECHNICAL FIELD

This invention relates to therapeutic-agent-containing medical devices, and more particularly, to medical devices having porous coatings which control therapeutic agent exposure and/or release.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

It is known that the sizes and shapes of pores within a porous material are related to the release rate of drugs from, and the access of bodily fluids to, that material. As a general rule, once pores are formed in a particular material, the pore size and shape are locked in.

SUMMARY OF THE INVENTION

According to an aspect of the invention, implantable or insertable medical devices are provided which contain the following: (a) one or more porous regions comprising pores and (b) one or more therapeutic agents which are (i) contained within the porous regions, (ii) disposed beneath the porous regions, or (iii) both. Moreover, the porous regions are capable of undergoing a change in configuration, such that the pores undergo a change in configuration, upon subjecting the porous regions to activating stimuli.

An advantage of the present invention is that medical devices may be provided in which the transport of species into the medical device, out of the medical device, or both, are tightly controlled, with therapeutic agent release potentially displaying zero order release kinetics.

Another advantage of the present invention is that implantable or insertable medical devices may be provided with porous regions whose pores have widths that may be expanded to facilitate loading of therapeutic agents (e.g., therapeutic agents for the treatment of restenosis, thrombus prevention, infection prevention, wound healing, etc.) and subsequently contracted in order to optimize therapeutic agent release.

Another advantage of the present invention is that implantable or insertable medical devices may be provided with porous regions whose pores have widths that are initially in an expanded state to initially facilitate biological access to immobilized therapeutic agents (e.g., enzymatic agents, bioactive agents, etc.) within the devices upon implantation or insertion of the device, which pores are subsequently contracted in vivo (e.g., with an external stimulus), thereby reducing access to the therapeutic agents.

Yet another advantage of the present invention is that implantable or insertable medical devices may be provided with porous regions whose pores have widths that are initially in a constricted state to initially restrict biological access to immobilized therapeutic agents within the devices upon implantation or insertion of the device, which pores are subsequently expanded in vivo, thereby facilitating access to the therapeutic agents.

These and other aspects, embodiments and advantages of the present invention will become immediately apparent to those of ordinary skill in the art upon review of the Detailed Description and Claims to follow.

DETAILED DESCRIPTION

Figure 1A:
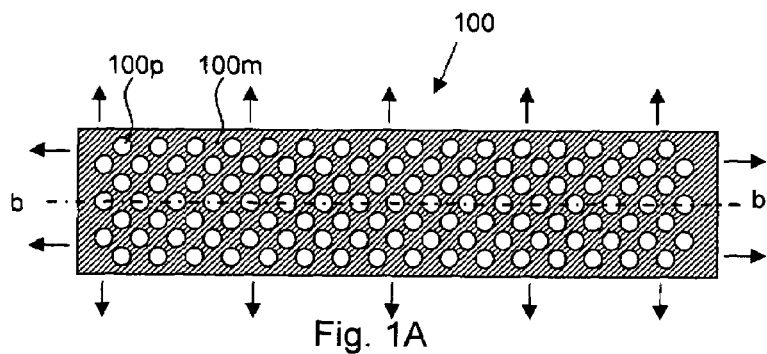
FIG. 1A is a schematic top view of a porous shape memory region in its permanent shape, in accordance with an embodiment of the present invention.

According to an aspect of the invention, implantable or insertable medical devices are provided which contain the following: (a) one or more porous regions comprising pores and (b) one or more therapeutic agents which are (i) contained within the porous region, (ii) disposed beneath the porous region, or (iii) both. Moreover, the porous regions are capable of undergoing a change in configuration, such that the pores undergo a change in configuration, upon subjecting the porous regions to activating stimuli. For example, the porous regions may have a shape memory such that the pores decrease or increase in width upon being subjected to a suitable shape memory activating stimuli.

The therapeutic agent may be, for example, releasably disposed or immobilized within the medical device. In either case, the porous region may allow transport of species (e.g., therapeutic agent, species from the bodily environment surrounding the device, catalytic products of such bodily species, etc.) to occur within the interior and/or exterior of the device. Depending upon the change in configuration that occurs, the porous region may present a greater barrier to transport (e.g., where the pores decrease in width) or a lesser barrier to transport (e.g., where the pores increase in width).

For example, a therapeutic agent within and/or beneath the porous region may be transported from the device and into a surrounding environment such that it is released in vivo. Such release may be, for example, reduced (e.g., where pores decrease in width, which may be stimulated, for example, ex vivo or in vivo) or increased (e.g., where pores increase in width, which may be stimulated, for example, ex vivo or in vivo).

In other examples, an in vivo species may be transported from a surrounding environment and into the device, for example, where it may bind to a therapeutic agent disposed within and/or beneath the porous region or where it may react with a therapeutic agent to form another species (e.g., a less detrimental or more beneficial species) which is then transported from the device and into the body. Such transport to (or to and from) the therapeutic agent may be, for example, decreased (e.g., where pores decrease in width) or increased (e.g., where pores increase in width), upon suitable stimulation in vivo or ex vivo.

Medical devices in accordance with the present invention vary widely and include numerous implantable or insertable medical devices, for example, stents (including coronary vascular stents, peripheral vascular stents, cerebral, urethral, ureteral, biliary, tracheal, gastrointestinal and esophageal stents), stent grafts, catheters (e.g., renal or vascular catheters such as balloon catheters and various central venous catheters), guide wires, balloons, filters (e.g., vena cava filters), vascular grafts, vascular access ports, embolization devices including cerebral aneurysm filler coils (including Guglilmi detachable coils and metal coils), myocardial plugs, patches, pacemakers and pacemaker leads, left ventricular assist hearts and pumps, total artificial hearts, heart valves, vascular valves, anastomosis clips and rings, and other prostheses, including tissue engineering scaffolds for cartilage, bone, skin and other in vivo tissue regeneration, among others.

The implantable or insertable medical devices of the present invention may perform one or more functions, including, for example, drug-delivery, mechanical, electrical, and/or magnetic functions, among others.

The medical devices of the present invention may be implanted or inserted within a variety of tissues or organs of a subject, including tumors, organs and organ systems including but not limited to the heart, coronary and peripheral vascular system (referred to overall as "the vasculature"), lungs, trachea, brain, liver, kidney, urogenital system (including, vagina, uterus, ovaries, prostate, bladder, urethra and ureters), eyes, ears, spine, nervous system, esophagus, intestines, stomach, and pancreas, skeletal muscle, smooth muscle, breast; cartilage, and bone. Preferred subjects (also referred to as "patients") are vertebrate subjects, more preferably mammalian subjects and more preferably human subjects.

In the medical devices of the present invention, transport of species is regulated, at least in part, by the porous regions. The pores of the porous regions may be, for example, parallel to one another, interconnected, or both. They may be regular (e.g., cylindrical, etc.) or irregular in geometry.

As used herein, a "microporous" region is one whose pores are predominantly micropores. As used herein, a "micropore" is a pore whose largest surface dimension (e.g., diameter for a cylindrical pore, width for a rectangular or ribbon-shaped pore, etc.) lies between 100 nm and 100 μm in length. As used herein, a "nanoporous" region is one whose pores are predominantly nanopores. As used herein, a "nanopore" is a pore whose largest surface dimension does not exceed 100 nm in length. Microporous regions may further comprise pores that are not micropores, and nanoporous regions may further comprise pores that are not nanopores.

Depending on the pore size, it is known that nanoporous regions having parallel or near parallel pore structures can release species, such as therapeutic agents, in accordance with zero order kinetics. In other less-structured release-controlling regions, the species may travel through the region via interconnected networks of pores. In some instances, the lateral dimensions (e.g., the radii) of the interconnected pores approach the lateral dimensions (e.g., the hydrated radius) of the species that is being transported. Consequently, the species may move within, and ultimately be released from, pores of these diameters (as opposed to being trapped by pores having smaller radii). In such instances, the interactions between the species and the walls of the nanopores can have a significant effect upon the transport that is observed. Indeed, as the diameter of the pore approaches the diameter of the species that is being transported, the surface interactions begin to dominate transport. See, e.g., Tejal A. Desai, Derek Hansford and Mauro Ferrari, "Characterization of micromachined silicon membranes for immunoisolation and bioseparation applications J. Membrane Science," 159 (1999) 221-231, which describes insulin release through silicone nanomembranes. As with parallel pore structures, the interconnected pore structures are capable of transporting species in a highly controlled manner, and they have the potential to approach zero order transport kinetics where pore diameters approach the size of the species that is being transported. The transport rate may also be affected by the depth and tortuousity of the pores within the interconnected porous network.

Of course, other release kinetics may be achieved with porous regions, including suitable members selected from first order, second order, step-wise and burst release kinetics, among others.

Pores may also promote cell adhesion. See, e.g., E. E. L. Swan, K. C. Popat, C. A. Grimes, T. A. Desai, "Fabrication and evaluation of nanoporous alumina membranes for osteoblast culture," *Journal of Biomedical Materials Research Part A*, Volume 72A, Issue 3, Pages 288-295, Published Online: 14 Jan. 2005, which describes osteoblast response to surface topography in anodized nanoporous alumina membranes.

Various examples of techniques which may be employed for forming porous regions, including microporous and nanoporous regions, are summarized below.

As is known, shape memory materials are stimuli-responsive materials that have the capability of changing their shape upon application of an external stimulus, such as thermal, electrical, solvent, pH, pressure, or light stimulus, or any other suitable stimulus. A change in shape caused by a change in temperature is called a thermally induced shape memory effect.

The present invention takes advantage of porous regions formed from such materials, for example, in order to modulate transport of various species (e.g., therapeutic agents, species from the bodily environment surrounding the device, catalytic products of such bodily species, etc.) to and from implantable or insertable medical devices, among other effects.

For example, therapeutic agent loading may be conducted while the porous region is in a temporary, deformed shape in which the widths of pores within the same are expanded, and thus transport of the therapeutic agent into and/or through the porous region is encouraged. Upon application of a suitable stimulus, however, the porous region (including the pores within the same) returns to an original, "remembered" shape, thereby reducing transport of species from the same.

The ability to contract the pore width (e.g., throughout the porous region, or primarily at the neck or external opening of the pores at the outer surface, etc.) so that they approach the size of the agent being released, would allow for tight control of the release profile; for example, a zero order profile may be achieved, which is independent of the concentration gradient and controlled by the interaction between the agent and the pore.

As another example, a medial device may be implanted or inserted into a patient which device contains an immobilized therapeutic agent (e.g., an enzymatic agent, bioactive agent, etc.), for instance, a therapeutic agent immobilized within a temporary, deformed porous region, immobilized beneath the porous region, or both. Upon application of a suitable stimulus in vivo to return the porous region to its original shape (which may shrink or enlarge the pores, as desired), transport of species (e.g., species from the bodily environment surrounding the device, catalytic products of such bodily species, etc.) to and from the device may be increased (upon enlargement of the pore widths in vivo or ex vivo) or may be decreased (upon shrinkage of the pore widths in vivo or ex vivo).

Porous regions for use in the present invention are not limited to any particular shape memory material. A few examples are discussed here, including various shape memory polymers and metals.

With shape memory polymers, the process of programming and recovery of a shape is generally as follows: (a) first, the polymer is conventionally processed to receive its original, or permanent, shape, (b) the polymer is then deformed and the intended temporary shape is fixed in a process called programming, which typically consists of heating the sample above a transition temperature, deforming it, and cooling it below the transition temperature while in the deformed state. The permanent shape is now stored while the sample shows the temporary shape. Subsequent heating of the shape memory polymer above the transition temperature leads to the recovery of the stored, permanent shape. Typically, upon cooling of the polymer, no recovery of the temporary shape is observed. This effect is known as a one-way shape memory effect. Dimensional changes within shape memory polymers may be on the order of, for example, 100-1000%. For example, segmented polyurethanes developed by Mitsubishi Heavy Industries in Nagoya, Japan are reported to have dimensional changes of about 200%. As another example, "Biodegradable Shape-Memory Polymer Developed," *European Medical Device Manufacturer*, September 2002 describes a biodegradable polymer developed by Andreas Lendlein and Robert Langer, which can achieve recoverable deformations of up to 1000% in some cases.

Specific examples of shape memory polymers include block copolymers and covalently linked polymer networks. These polymers may exhibit a shape memory functionality by using the polymer chains as a type of molecular switch. One possibility for a switch function is a thermal transition of the chains in the temperature range of interest for a particular application (e.g., between room and body temperature, etc.). At temperatures above the thermal transition temperature ($T_{trans}$) the chain segments become more flexible, whereas the flexibility of the chains below this thermal transition is at least partly limited.

Phase-segregated multiblock copolymers, commonly linear block copolymers, are known to display at least two separated phases. The phase showing the highest thermal transition $T_{perm}$ (sometimes referred to as the hard phase) provides physical cross-links (also referred to sometimes as "physical netpoints") and is responsible for the permanent shape of the material. (Above this temperature the polymer commonly melts and can be processed by conventional processing techniques such as extrusion, injection molding, melt spinning, etc.) The portion of the block copolymer that forms the hard phase is sometimes referred to as the hard segment. A second phase (i.e., a switching phase) enables the fixation of the temporary shape. The portion of the block copolymer that forms the switching phase is sometimes referred to as the switching segment. The transition temperature ($T_{trans}$) for the fixation of the switching phase is typically either a glass transition temperature ($T_g$) or a melting temperature ($T_m$). In the case of a melting temperature, one observes a relatively sharp transition in most cases, whereas glass transitions typically extend over a broader temperature range. After applying a force that is sufficient to deform the material at a temperature above $T_{trans}$ but below $T_{perm}$, a temporary shape is achieved, which can be fixed by cooling the polymer below $T_{trans}$ while continuing to apply the deformation force. The deformation force may then be removed. Subsequent heating of the material above $T_{trans}$ returns the material to its permanent shape.

Specific examples of known multiblock copolymers with $T_{trans}=T_{melt}$ include (a) multiblock copolymers of polyurethanes with poly(ϵ-caprolactone) switching phases, for example, polyesterurethanes such as those with a hard phase segment based on methylenebis(4-phenylisocyanate) (MDI) and 1,4-butanediol, and with a switching phase segment based on poly(ϵ-caprolactone) having a number-average molecular weigh ($M_n$) between 1600 and 8000, for which the switching temperature for the shape memory effect may vary, for example, between 44 and 55° C., depending on the weight fraction of the switching segments and the molecular weight of the switching segments, (b) block copolymers with a hard phase segment based on polyethylene terephthalate (PET) and switching phase segment based on polyethylene oxide (PEO), for which the thermally induced shape memory effect is triggered by the melting temperature of the PEO crystallites and may vary, for example, between 40 and 60° C. depending on the molecular mass of the PEO blocks and on the PET content, (c) block copolymers with a hard phase segment based on polystyrene and switching phase segment based on poly(1,4-butadiene), for which the thermally induced shape memory effect is triggered by the melting temperature of the poly(1,4-butadiene) and may vary, for example, from between 45 and 65° C., (d) ABA triblock copolymers having a central poly(tetrahydrofuran) block (B block) with number-average molecular weight between 4100 and 18800 and having terminal poly(2-methyl-2-oxazoline) blocks (A blocks)

with molecular weights of 1500, for which the A blocks exhibit glass transition temperatures around 80° C. and represent the hard phase segment, and for which the thermally induced shape memory effect is triggered by the melting temperature of the B blocks and may vary, for example, between 20 and 40° C., and (e) biodegradable block copolymers having at least one hard phase segment such as poly(p-dioxanone) and at least one amorphous switching phase segment such as ε-caprolactone ($T_m$=46-64° C.).

Specific examples of multiblock copolymers with $T_{trans}$=$T_g$ include (a) polyurethanes with polyether switching phase segments, for example, polyetherurethanes such as those with a hard phase segment formed from methylenebis(4-phenylisocyanate) (MDI) and 1,4-butanediol, and a switching phase segment formed from tetrahydrofuran ($M_n$=250-2900), for which the thermally induced shape memory effect may vary, for example, from −56 to 54° C., (b) polyurethanes with polyester switching phase segments, for example, polyesterurethanes such as those with a hard phase segments synthesized from MDI and 1,4-butanediol and a switching phase segment formed from poly(ethylene adipate), for which the glass transition temperatures obtained with switching segments having weight average molecular weights of 300, 600, and 1000 at a constant hard segment content of 75 mol % decreases from 48 to −5° C. with increasing molecular weight of the poly(ethylene adipate) segments, and for which glass transition temperatures obtained with a switching phase segment with a weight average molecular weight of 600 increases from 13 to 35° C. as the hard-segment content increases from 75 to 90 mol %, (c) a series of block copolymers described in U.S. Pat. No. 5,128,197 to Mitsubishi Heavy Industries, which may have glass transition temperatures in the range of form −45 to 48° C., and (d) biodegradable block copolymers having at least one hard segment such as poly(p-dioxanone) and at least one amorphous switching segment such as poly(1-lactide)-co-glycolide ($T_g$=35-50° C.).

Other examples of shape memory polymers include (a) polynorbornene such as NORSOREX, a linear, amorphous polynorbornene developed by CdF Chemie/Nippon, having a molecular weight of about three million, having about 70 to 80 mol % of trans-linked norbornene units, and having a glass transition temperature between 35 and 45° C. (the material softens abruptly above the glass transition temperature $T_g$, and if the chains are stretched quickly in this state, and the material is rapidly cooled down again, it is possible to freeze the induced elastic stress within the material) and (b) polyethylene grafted with nylon-6, in which the nylon-6 hard-segment content is between about 5 and 20 wt %, and in which the remaining polyethylene segments provide the thermally induced shape memory effect which corresponds to the melting point of the PE crystallites of 120° C.

Unlike the physical crosslinks for the above copolymers, the permanent shape of shape memory polymer networks are stabilized via covalent crosslinks. Besides the crosslinks, such networks also generally contain flexible components in the form of amorphous chains. If the working temperature is above the $T_{trans}$ for these chains, the networks will be elastic. As with shape memory block copolymers, the $T_{trans}$ thermal transition chosen for the fixation of the temporary shape may be a melting point or a glass transition temperature. After deforming the material at a temperature above the $T_{trans}$, the temporary deformed shape can be fixed by cooling the polymer below $T_{trans}$. Subsequent heating of the material above $T_{trans}$ returns the material to its permanent shape.

Certain hydrogels, such as hydrogels formed from copolymerized acrylic acid and stearyl acrylate, cross-linked with methylenebisacrylamide, are known to show a strong shape memory effect. Below about 25° C. these polymers behave like tough polymers, while above about 50° C. softening enables the materials to be stretched significantly by a deformation force. The stretched shape can be maintained by continuing to apply the deformation force during the cooling process. When the material is heated up again above the transition temperature the one-way shape memory effect takes place and the external shape in which the material was produced initially is recovered. The permanent shape is predetermined by the covalent polymer network.

Further information on shape memory polymers, such as shape memory gels, block copolymers and covalently cross-linked shape polymer networks, including biodegradable covalently cross-linked shape polymer networks, can be found, for example, in A. Lendlein and S. Kelch, "Shape Memory Polymers" *Angew. Chem. Int. Id.* 2002, 41, 2034-2057 and the references cited therein.

Of the various shape memory metals and alloys, those nickel-titanium alloys known as "NiTinol," are perhaps the best known. NiTinol shape memory alloys can exist in a two different temperature-dependent crystal structures (phases) called martensite (lower temperature phase) and austenite (higher temperature or parent/permanent phase). When martensite NiTinol is heated, it begins to change into austenite. The temperature at which this phenomenon starts is called austenite start temperature ($A_s$). The temperature at which this phenomenon is complete is called austenite finish temperature ($A_f$). On the other hand, when austenite NiTinol is cooled, it begins to change onto martensite. The temperature at which this phenomenon starts is called martensite start temperature ($M_s$). The temperature at which martensite is completely reverted is called martensite finish temperature ($M_f$). Composition and metallurgical treatments can impact these temperatures.

NiTinol is well known for its shape memory and superelastic (or pseudoelastic) properties. When the material is in its martensite form, it is soft and ductile and can be easily deformed, while superelastic NiTinol is highly elastic (rubber-like), and austenitic NiTinol is quite strong and hard (similar to titanium). The NiTinol material has all of these properties, with their specific expression depending on the temperature environment in which it is used.

Generally, the shape memory effect allows the alloy to be (a) provided in a first shape while in the relative high-temperature austenite phase, (b) cooled below a transition temperature range, for example, from $M_s$ down to $M_f$ or below, whereupon the austenite is partially (between $M_s$ and $M_f$) to completely (at $M_f$ or below) transformed into the relative low-temperature martensite phase, (c) deformed while in a martensite phase into a second configuration, and (d) heated back to the austenite transition temperature range, specifically from $A_s$ up to $A_f$ or above, such that the alloy transforms partially (between $A_s$ and $A_f$) to completely (at $A_f$ or above) from the second configuration back to the first configuration. This is called one-way shape memory.

Superelasticity refers to the ability of NiTinol to return to its original shape upon unloading after a substantial deformation. This is based on stress-induced martensite formation. The application of an outer stress to an austenite sample causes martensite to form at temperatures higher than $M_s$. The macroscopic deformation is accommodated by the formation of martensite. When the stress is released, the martensite transforms back into austenite and the specimen returns back to its original shape. The highest temperature at which martensite can no longer stress induced is called $M_d$. Superelasticity typically appears in a temperature range from near $A_f$ and up to $M_d$. NiTinol in this temperature range is thus suitable for applications requiring recoverable deformation. For example, conventional pseudoelastic NiTinol is useful for applications requiring recoverable strains of up to 8% or more. For further information, see, e.g., U.S. Pat. No. 6,540,849 to DiCarlo et al., and the references cited therein.

Figure 1B:
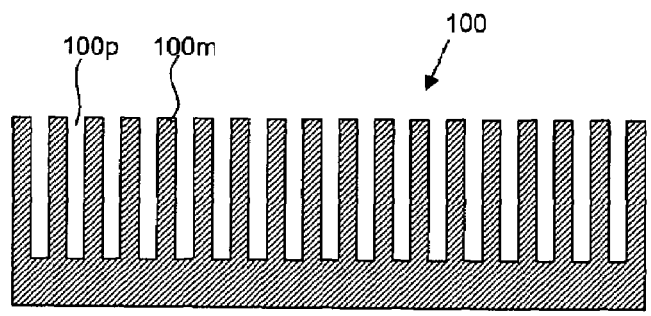
FIG. 1B is a cross sectional view of the porous shape memory region of FIG. 1A, taken along line b-b.

A specific embodiment of the invention will now be described with reference to FIGS. 1A-4B. FIG. 1A is a schematic top view of a porous region 100 which consists of a shape memory material 100m, such as a shape memory polymer or shape memory metal, which has been processed such that a plurality of pores 100p are formed therein. FIG. 1B is a cross sectional view of the porous region 100 of FIG. 1A, taken along line b-b. This is the permanent or "remembered" shape of the material.

Figure 2A:
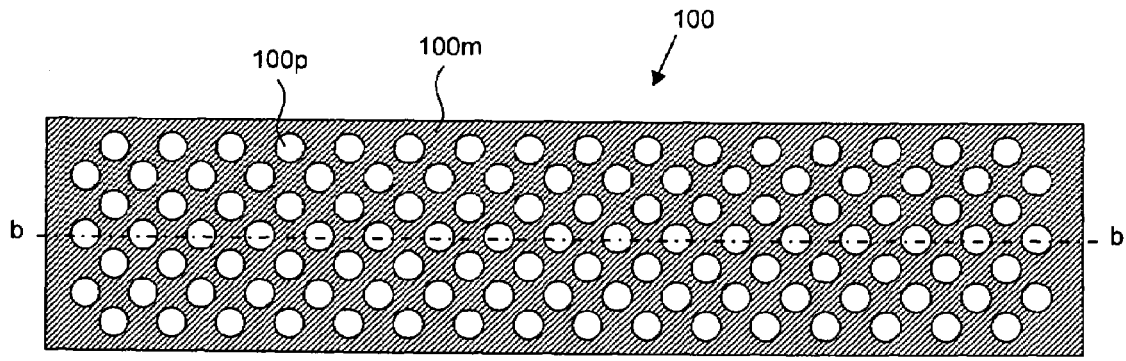
FIG. 2A is a schematic top view of the porous shape memory region of FIG. 1A after being deformed into its temporary shape, in accordance with an embodiment of the present invention.
Figure 2B:
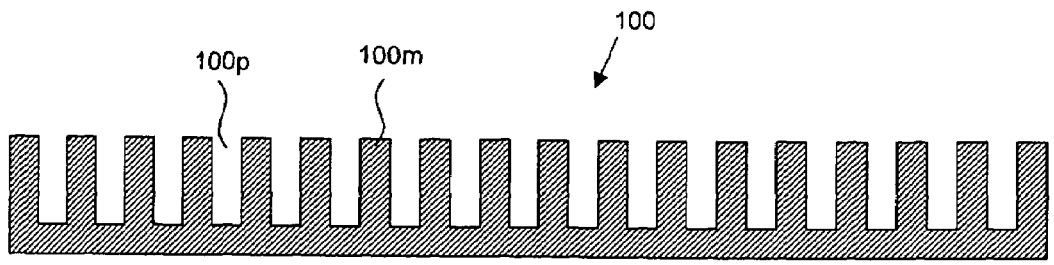
FIG. 2B is a cross sectional view of the porous shape memory region of FIG. 2A, taken along line b-b.

For example, in the case where the material is a shape memory polymer, the material may be initially processed below its transition temperature to yield the porous structure of FIGS. 1A-1B. The material is then typically heated above its transition temperature and deformed, for example, by stretching the porous region outward along its perimeter as illustrated by the arrows in FIG. 1A. This results in a widening of the pores 100p and an increase in the area of the porous region 100 when viewed in top view, as illustrated in FIG. 2A, while also resulting in a decrease in the thickness of the material when viewed in cross-section, as illustrated in FIG. 2B. This temporary shape is then fixed by cooling the material to below the transition temperature, at which point the deformation force may be removed.

A specific example of such a shape memory polymer material is the Veriflex™ shape memory polymer resin system, a crosslinked, two-component, styrene-based thermoset resin available from CRG Industries, LLC (a spin-off of Cornerstone Research Group, both of Dayton, Ohio, USA). The two-part resin becomes a rigid polymer when mixed and cured, but if heated above its activation temperature of 85° C. (185° F.), it becomes elastic and can be reshaped and stretched, elongating as much as 200 percent. When cooled, it retains its deformed shape, but when reheated it returns to its original shape. This cycle can be repeated numerous times. The polymer is also available composite form with woven materials under the brand name Veritex™. Another example of such a material is available from Composite Technology Development (CTD) Inc., Lafayette, Colo., USA. In particular, the company's Tembo™ Elastic Memory Composite material is based on epoxy and cyanate ester, and is reported to tolerate reinforcement with carbon or other fibers at loadings to 40%. Another commercially available family of shape memory polymer are Calo.MER™ polyurethane-based shape-memory thermoplastics available from The Polymer Technology Group, Berkeley, Calif., USA. Block and segmented copolymers suitable for use as shape-memory thermoplastics including polyetherurethanes, polyesterurethanes, poyetherpolyesters, polyetherpolyamides, with polyether or polyester soft segments, among others. Further shape memory polymers have been reported which are based on polyethylene terephthalate and nylon 6. See P. A. Toensmeier, "Shape Memory Polymers Reshape Product Design," *Plastics Engineering*, Mar. 10-11, 2005.

In the alternative case where the material is a shape memory metal such as NiTinol, the porous material 100 of FIGS. 1A-1B may represent the material while in its permanent or austenite phase. The porous material 100 is cooled to a temperature below the martensitic phase transformation start temperature $M_s$ (e.g., a NiTinol material may have, for instance, an $M_s$=−50° C., $A_s$=25° C. and $A_f$=33° C.). If practical, the porous material 100 may be taken down to the martensitic phase transformation finish temperature $M_f$. At this temperature and at any temperature above this temperature but below the austenitic phase transformation start temperature $A_s$, the porous region 100 will be relatively soft and thus relatively easy to deform, for example, able to be stretched along the lines discussed above, until the pores are deformed as illustrated in FIGS. 2A-2B.

A specific example of a commercially available porous NiTinol material is that available from Biorthex, Inc., Blainville, Quebec, Canada, under the trade name Actipore™. It has a porous structure made of interconnected passageways, with an approximate porosity of 65% and an ideal average pore size of 215 microns.

Regardless of the shape memory material, the pores 110p are now wider at the surface (in particular, the diameter is greater in the embodiments illustrated in FIGS. 2A and 2B), thus making it easier to load them with therapeutic agent. For example, the pores 100p of the porous region 100 may be at least partially filled with a therapeutic agent 110 as illustrated in the top and cross-sectional schematic views of FIGS. 3A and 3B, respectively.

Various methods are available for loading the pores of the porous region. For instance, a fluid containing dissolved or dispersed therapeutic agent (and suitable supplemental material(s), if desired) may be contacted with the porous region 100, for instance, by dipping, spraying, coating with an applicator (e.g., by roller or brush), spin-coating, web coating, techniques involving coating via mechanical suspension including air suspension, ink jet techniques, and combinations of these processes, among other techniques. Water, organic solvents, subcritical fluids, critical point fluids, supercritical fluids, and so forth can be used as carriers for the therapeutic agent. Further information on supercritical solvent loading may be found in Ser. No. 11/007,866, filed 9 Dec. 2004 and entitled "Use of Supercritical Fluids to Incorporate Biologically Active Agents into Nanoporous Medical Articles."

Figure 3A:
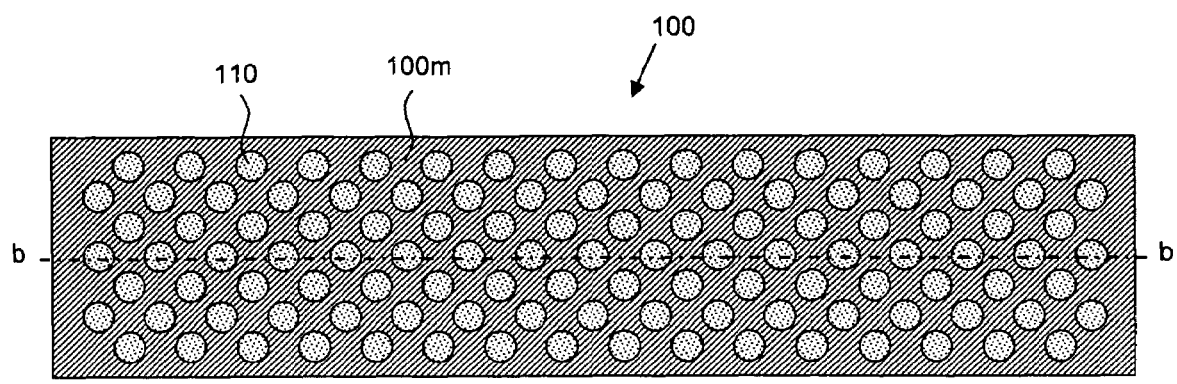
FIG. 3A is a schematic top view of the porous shape memory region of FIG. 2A after being loaded with a therapeutic agent, in accordance with an embodiment of the present invention.
Figure 3B:
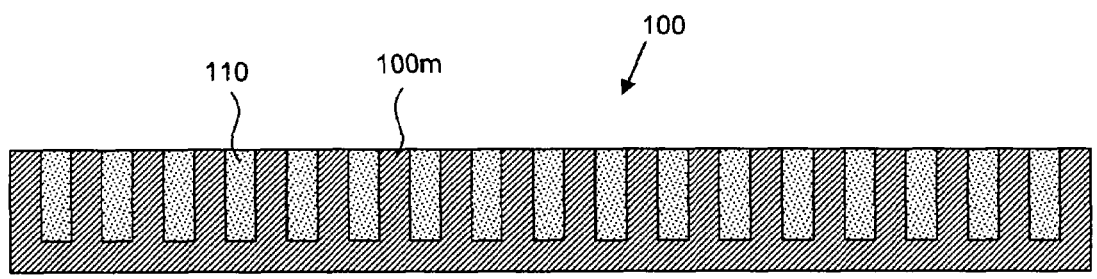
FIG. 3B is a cross sectional view of the porous shape memory region of FIG. 3A, taken along line b-b.
Figure 4A:
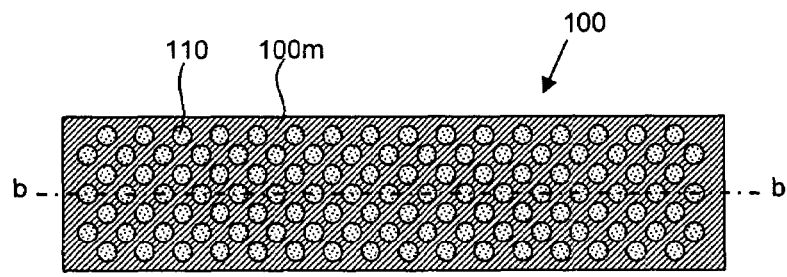
FIG. 4A is a schematic top view of the loaded porous shape memory region of FIG. 3A after the porous shape memory region is returned to its permanent shape, in accordance with an embodiment of the present invention.
Figure 4B:
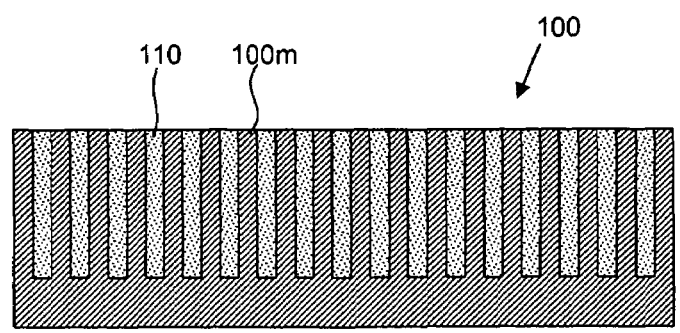
FIG. 4B is a cross sectional view of the porous shape memory region of FIG. 4A, taken along line b-b.

The therapeutic-agent-containing porous region 100 of FIGS. 3A-3B is then stimulated (e.g., heated) for example, either ex vivo or in vivo (e.g., where the body temperature is sufficiently high or where the porous region is heated in vivo, for example, using a catheter having a heating element or by heating the material using MRI). Due to the shape memory character of the material 100m in FIGS. 3A-3B, the material 100m, along with the pores formed therein (now loaded with therapeutic agent 110) return to their earlier dimensions as illustrated in the top and cross-sectional schematic views of FIGS. 4A and 4B, respectively.

As noted above, in the case of a shape memory polymer, the material is typically heated to a temperature above the transition temperature, which leads to the recovery of the stored, permanent shape. In the case of a shape memory metal, the porous material 100 is typically heated back to the austenite phase (e.g., to $A_s$ or above, preferably $A_f$ or above), such that the alloy transforms from the martensite phase back to the austenite phase to recover the stored, permanent shape.

For example, where the therapeutic agent is immobilized within the porous region, transport into the device of species from the bodily environment surrounding the device (as well as transport of products of such bodily species, e.g., catalytic products, etc., from the device) will be slowed. Where the therapeutic agent is releasably disposed within the porous region, on the other hand, transport of the therapeutic agent from the device into the bodily environment surrounding the device will be slowed.

Figure 5A:
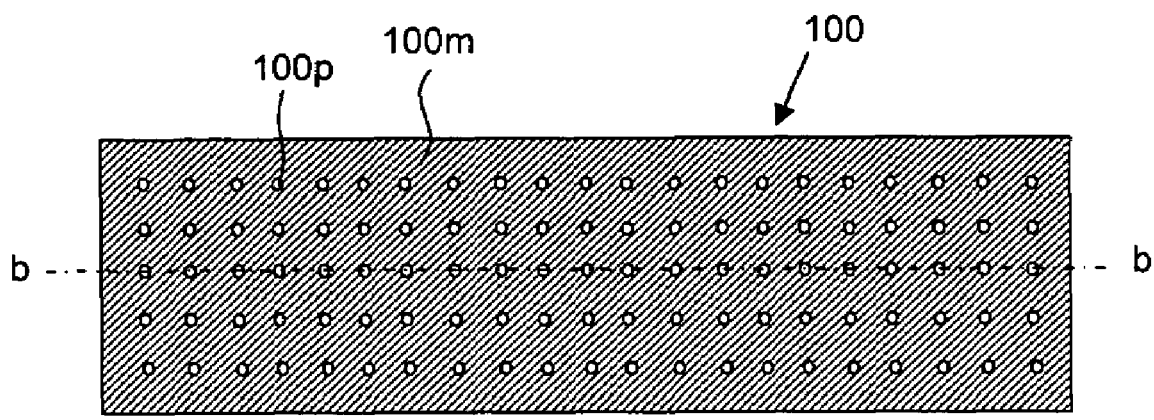
FIG. 5A is a schematic top view of a porous shape memory region, in accordance with an embodiment of the present invention.
Figure 5B:
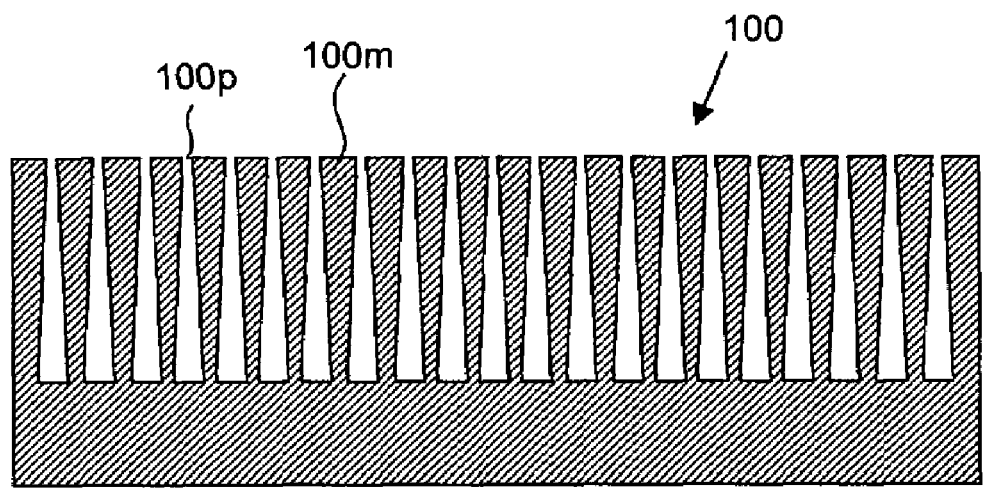
FIG. 5B is a cross sectional view of the porous shape memory region of FIG. 5A, taken along line b-b.
Figures 6A, 6B, 6C:
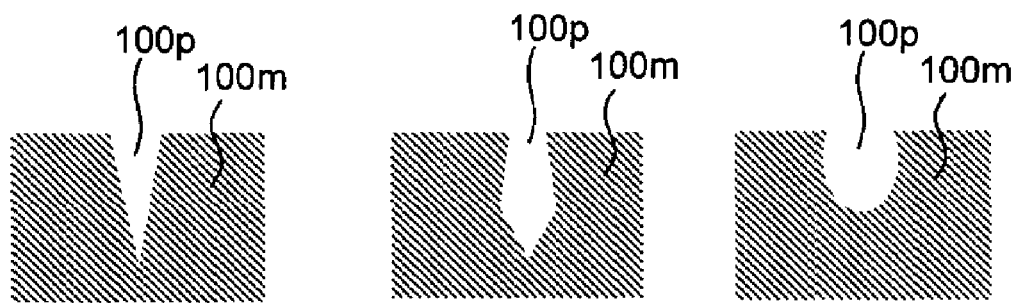
FIGS. 6A-6C are schematic cross sectional views of various pore configurations, in accordance with certain embodiments of the present invention.

While the pores in FIGS. 1A-4B are cylindrical, a variety of non-cylindrical pore shapes may be employed, such as the pores of partial conic character illustrated in the top and cross-sectional schematic views of FIGS. 5A and 5B, respectively. Further examples include other pores with polygonal cross-sections, including trilateral (see, e.g., FIG. 6A), and pentalateral (see, e.g., FIG. 6B) cross-sections, semicircular and semi-oval cross-sections (see, e.g., FIG. 6C), as well as other regular and irregular cross-sections.

Various examples of techniques which may be employed for forming porous regions, including microporous and nanoporous regions, within various shape memory materials will now be described.

In some embodiments, molding techniques may be employed in which a mold is provided with numerous protrusions, which create pores upon casting a shape memory material into the same.

In some embodiments, a solid precursor region is formed, which is subsequently converted into a porous region. These methods include the following, among others: (a) direct-write techniques, for example, (i) techniques in which pores are created through contact with solid tools, for instance, micro-drilling, micromachining, etc. techniques, using high precision equipment such as high precision milling machines and lathes, and (ii) techniques that form pores without the need for solid tools, for instance, those based on directed energetic beams such as laser, electron, and ion beams, and (c) mask-based techniques, for example, (i) techniques in which the masking material does not contact the layer to be machined, but which is provided between a directed source of excavating energy and the material to be machined, such as opaque masks having apertures formed therein, semi-transparent masks such as gray-scale masks, and so forth, and (ii) techniques in which the masking material contacts the substrate to be processed, such as masks that are formed using known lithographic techniques.

For example, a mask with micro- or nano-scale apertures may be formed on a precursor region using known lithographic techniques, including optical, ultraviolet, deep ultraviolet, electron beam, and x-ray lithography. The material may then be subjected to further processing such as wet or dry (plasma) etching to yield a micro- or nano-porous region. (As indicated above, nanoporous regions may be desirable, for example, where one wishes to approach or achieve a zero order release profile.) For instance, an isotropic or partially isotropic etching process may be employed to produce pores with an undercut structure (see, e.g., the cross-section of FIG. 6C) whereas an anisotropic etching process may be employed to produce pores with more linear (e.g., vertical) sidewalls.

In this regard, it is noted that there is a great amount of available know-how in the semiconductor industry for etching holes (e.g., vias), trenches and other depressions in various materials, including metallic and polymeric materials.

In some embodiments, a precursor region is formed which comprises first and second materials. Subsequently, the precursor region is subjected to conditions where the first material is either reduced in volume or eliminated from the precursor region. By providing micro- or nano-domains of the first material within the precursor region, a micro- or nanoporous region may be formed. Materials for forming such removable or size-reducible domains include, among others, the following: (a) materials that are converted into gaseous species upon heating, for example, materials that sublime, materials that melt and then evaporate, and materials that form gaseous reaction products such as combustible materials, (b) metal oxides which may be reduced to their corresponding metal, resulting in a loss in volume, (c) materials which are dissolved or otherwise removed in a solution.

For example, Ni—Ti may be provided with a third removable (e.g., less noble) material and domains of the third material subsequently oxidized and removed (e.g., by contact with an appropriate acid such as nitric acid, by application of a voltage of sufficient magnitude and bias during immersion in a suitable electrolyte, by heating in the presence of oxygen, followed by dissolution of the resultant oxide, and so forth). This process is sometimes referred to as dealloying. As an example of a process for forming a porous, shape memory polymer, a block copolymer with a degradable block, a moderate Tg block and a high Tg block may be used to form a precursor region, after which the degradable block is removed.

Further methods may be used in the formation of porous shape memory materials. For example, porous NiTinol may be formed by plasma ion implantation. See N. Shevchenko et al., "Porous surface of NiTi alloy produced by plasma ion implantation," E-MRS 2005 Spring Meeting, May 31-Jun. 3, 2005, Strasbourg, France. As another example, porous NiTinol can be fabricated using spark plasma sintering of NiTinol powders. See, e.g., S. Nemat-Nasser et al., "Experimental characterization and micromechanical modeling of superelastic response of a porous NiTi shape-memory alloy," *Journal of the Mechanics and Physics of Solids*, 53 (2005) 2320-2346. Examples of further methods of forming porous shape memory polymers include polymer processing techniques in which a gas is introduced into a mold during processing (like those processes used in the creation of Styrofoam®) and techniques where supercritical fluid is introduced into polymers during processing.

In some embodiments, porous regions in accordance with the present invention are formed from microfibers or nanofibers. As used herein, a "microfiber" is a fiber whose largest axial cross-sectional dimension (e.g., diameter for a cylindrical fiber, width for a ribbon-shaped fiber, etc.) lies between 100 nm and 100 μm in length. As used herein, a "nanofiber" is a fiber whose largest axial cross-sectional dimension does not exceed 100 nm in length. Such fibers may be formed into porous regions using woven or nonwoven techniques.

Figure 7A:
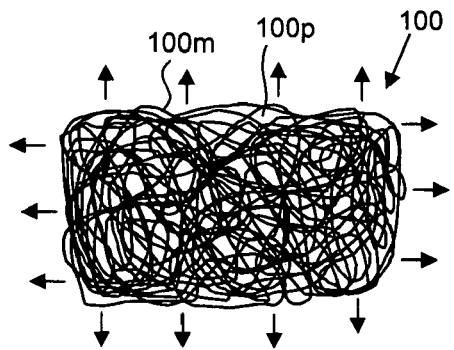
FIG. 7A is a schematic top view of a substantially planar (e.g., sheet-like) porous region.

For example, FIG. 7A is a schematic top view of a substantially planar (e.g., sheet-like) porous region 100, which consists of fibers of a shape memory material 100*m*, such as a shape memory polymer or shape memory metal, which are provided in a non-woven mass and which contains numerous pores 100*p* of irregular size and shape.

In the case of a polymer shape memory material, for example, the fiber may be extruded using a melt spinning or dry spinning process. In melt spinning, polymers are heated to a melt temperature prior to extrusion. By controlling the cooling parameters the extruded fibers may retain significant tack such that overlapping fibers become bonded to each other at various locations where the fibers intersect or otherwise contact each other. Alternatively (or as a further process step), the porous region 100 may be heated, and optionally pressed, in order to further consolidate the fiber(s) forming the same. In solvent spinning, on the other hand, polymers are dissolved in a solvent prior to extrusion. Analogous to melt spinning, by controlling the solvent removal parameters (e.g., drying environment, solution concentration, etc.) sufficient solvent may remain in the fibers such that overlapping fibers become bonded to each other at various locations where the fibers intersect or otherwise contact each other. Alternatively (or as a further process step), a solvent may be applied to the structure after formation (e.g., by spraying or quickly dipping such that the structure does not dissolve), and the porous region 100 optionally pressed, in order to further consolidate the fiber(s) forming the same.

Whether melt-spun, solvent-spun, or otherwise formed, the porous region 100 may then be heated above the transition temperature of the shape memory polymer, stretched (e.g., as illustrated by the arrows in FIG. 7A), and then cooled below the transition temperature while continuing to apply the stretching force, to yield the structure schematically illustrated in FIG. 7B.

In the case where the shape memory material 100m is a metallic shape memory material, a porous region 100 like that illustrated in FIG. 7A may be formed, for example, from NiTinol fibers. The porous region 100 may be heated and optionally pressed, in order to further consolidate the fiber(s) forming the same. In these embodiments, the porous material 100 of FIG. 7A corresponds to the material 100m while in its permanent or austenite phase. The porous material 100 is then cooled to at least below the martensitic phase transformation start temperature $M_s$ (and down to the martensitic phase transformation finish temperature $M_f$, if practical). At this temperature and at any temperature above this temperature but below the austenitic phase transformation start temperature $A_s$, the porous region 100 will be relatively soft and thus relatively easy to deform, for example, by stretching along the lines discussed above, until the pores are enlarged as illustrated in FIG. 7B.

Figure 7B:
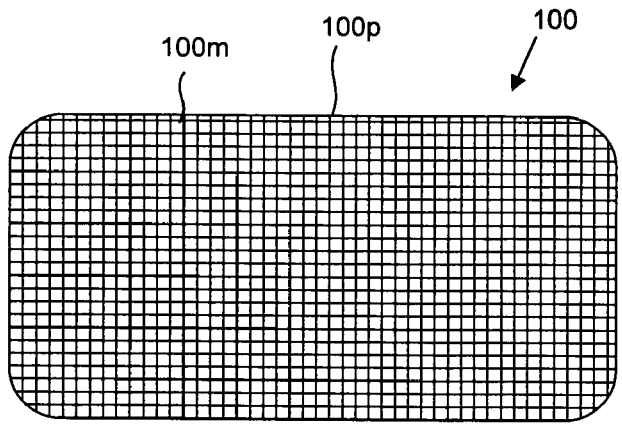
FIG. 7B is a schematic top view of the porous region of FIG. 7A after processing.

Regardless of whether a shape memory polymer or metal is employed, the resulting porous region 100 of FIG. 7B has an increased area (when viewed in top view) relative to that of FIG. 7A, and there is a narrowing of the fibrous material 100m as well as a widening of the pores 100p. Moreover, it is noted that when a substantially planar fibrous structure such as that of FIG. 7A is stretched as illustrated by the arrows in FIG. 7A the fibers within the structure tend to align somewhat with one another within the structure. (In this regard, FIG. 7B is a highly idealized structure, and arrangement of the fibers in the actual structure will be more randomly disposed than illustrated.)

Analogous to the embodiment of FIGS. 3A-3B above, the pores 100p of the porous region 100 may then be at least partially filled with a therapeutic agent. Moreover, analogous to the embodiments of FIGS. 4A-4B above, upon application of appropriate stimulus, the fibers 100m may attain their post shape memory configuration once again, becoming shorter, thicker and more randomly arranged as illustrated in FIG. 7A, albeit now containing a therapeutic agent, thereby reducing the pore width and retarding release.

In certain embodiments, it may be desirable to provide a porous shape memory layer over part or all of an underlying substrate, for instance, a substrate corresponding to one of the medical devices set forth above (e.g., stents and balloons, among many others). For example, it may be desirable to form a porous shape memory material layer on a substrate, or it may be desirable to first form a porous shape memory material layer and then attach it to a substrate, for example using a suitable adhesive.

By first forming a multiple porous shape memory material layers and then attaching them to a substrate, it may be possible, for example, to provide one or more first porous shape memory material layers loaded with a first therapeutic agent and one or more second porous shape memory material layers filled with a second therapeutic agent that differs from the first therapeutic agent.

A wide range of substrate materials may be provided for such purposes, including (a) organic materials (e.g., materials containing 50 wt % or more organic species) such as polymeric materials and (b) inorganic materials (e.g., materials containing 50 wt % or more inorganic species), such as metallic materials (e.g., metals and metal alloys) and non-metallic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals (e.g., metals such as gold, iron, niobium, platinum, palladium, iridium, osmium, rhodium, titanium, tantalum, tungsten, ruthenium, and magnesium), metal alloys comprising iron and chromium (e.g., stainless steels, including platinum-enriched radiopaque stainless steel), alloys comprising nickel and titanium (e.g., NiTinol), alloys comprising cobalt and chromium, including alloys that comprise cobalt, chromium and iron (e.g., elgiloy alloys), alloys comprising nickel, cobalt and chromium (e.g., MP 35N) and alloys comprising cobalt, chromium, tungsten and nickel (e.g., L605), alloys comprising nickel and chromium (e.g., inconel alloys), and alloys of magnesium and iron (e.g., their alloys with combinations of Ce, Ca, Zn, Zr and Li).

Specific examples of organic materials include polymers (biostable or biodegradable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above.

In some embodiments, a porous shape memory layer may be formed over (or first formed and then attached over) one or more depressions within a substrate, which may or may not contain a therapeutic agent at the time of formation (or attachment) of the porous shape memory layer. The depressions may come in various shapes and sizes and can extend partially or completely through the substrate. Commonly, the depressions may have smallest lateral dimensions (e.g., the diameter for a cylindrical depression, the width for an elongated depression such a trench, etc.) that are less than 1 mm (1000 µm), for example, ranging from 1000 µm to 500 µm to 250 µm to 100 µm to 50 µm to 10 µm to 5 µm to 2.5 µm to 1 µm or less.

Figure 8:
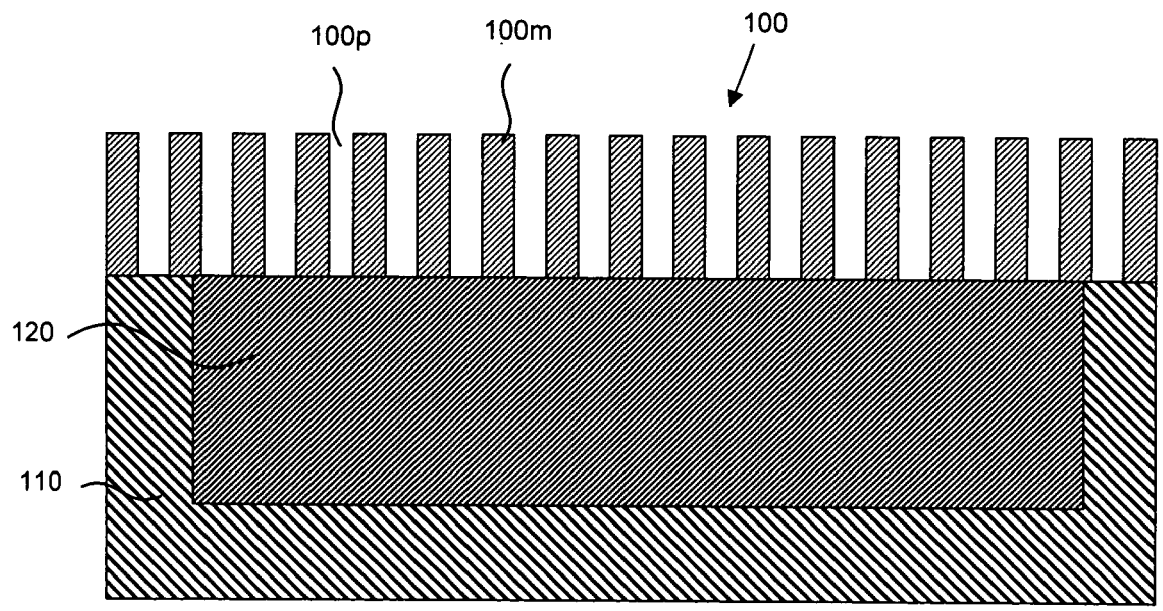
FIG. 8 is a schematic cross-sectional view of a medical device region that includes a porous shape memory region disposed over a substrate, which contains a therapeutic agent filled depression, in accordance with an embodiment of the present invention.

FIG. 8 is a schematic cross-sectional view of a medical device region 100 that includes a shape memory region 100m having pores 100p, disposed over a substrate 110, which contains a therapeutic-agent-filled depression 120, in accordance with an embodiment of the present invention. Of course, multiple depressions 120 may be provided as described further below. In this manner, it may be possible, for example, to provide different therapeutic agents at different locations on the medical device. For example, one may provide one or more first depressions filled with a first therapeutic agent (e.g., an antithrombotic agent at an inner, luminal surface of a stent), and one or more second depressions filled with a second therapeutic agent that differs from the first therapeutic agent (e.g., an antiproliferative agent at an outer abluminal surface).

Figure 9:
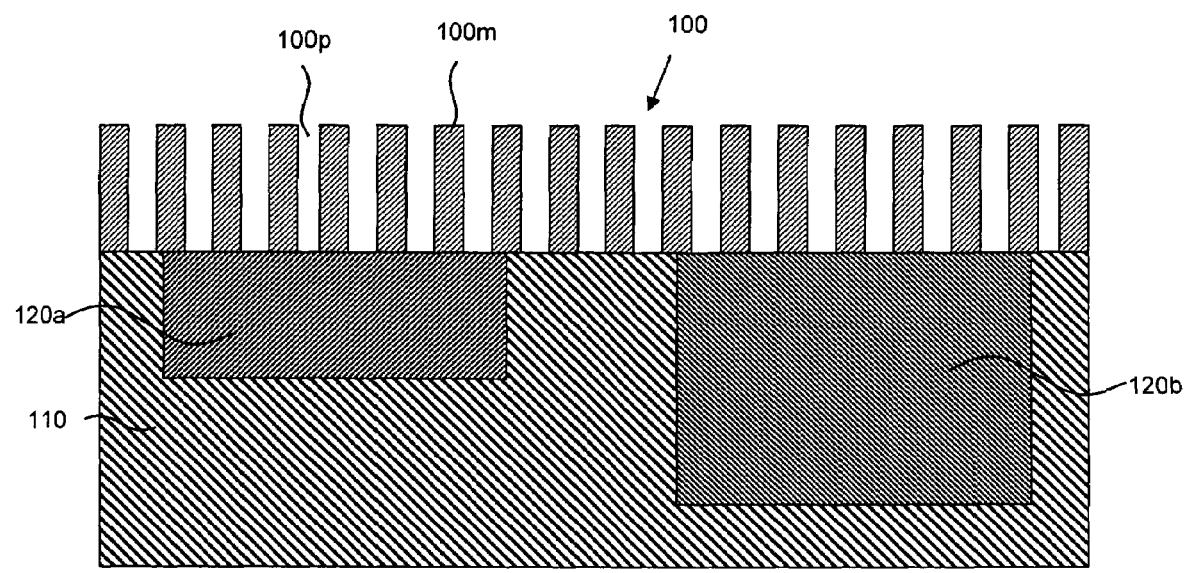
FIG. 9 is a schematic cross-sectional view of a medical device region that includes a porous shape memory region disposed over a substrate, which contains multiple therapeutic agent filled depressions, in accordance with an embodiment of the present invention.

In this regard, see, e.g., FIG. 9, which illustrates a schematic cross-sectional view of a medical device region 100 that includes a shape memory region 100m having pores 100p, disposed over a substrate 110, which contains multiple therapeutic-agent-filled depressions 120a, 120b, in accordance with an embodiment of the present invention. The depressions 120a, 120b may contain the same or differing therapeutic agents, they may be of the same or differing shapes, they may be of the same or differing sizes, and so forth.

Analogous to the examples presented above, the porous shape memory layer(s) overlying the depressions act(s) to regulate transport of species between the therapeutic-agent-containing depressions and the exterior environment, for example, increasing or decreasing transport upon application of a suitable stimulus.

Moreover, the pore sizes within the shape memory layer(s) can be tailored to the therapeutic agent. For example, where different therapeutic agents are provided at different locations on the medical device, pore sizes can be selected to provide short-term, intermediate-term or long-term release, as desired.

Figure 10:
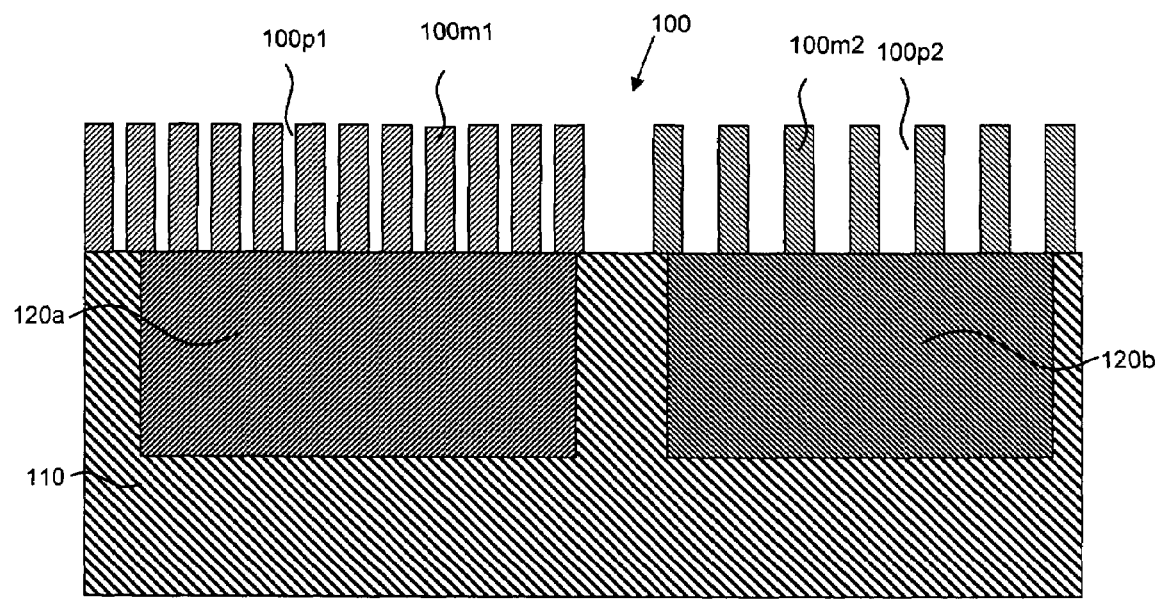
FIG. 10 is a schematic cross-sectional view of a medical device region that includes multiple porous shape memory regions disposed over a substrate, which contains multiple therapeutic agent filled depressions, in accordance with an embodiment of the present invention.

Turning now to FIG. 10, there is shown a schematic cross-sectional view of a medical device region 100 that includes a first shape memory region 100m1 having pores 100p1 and a second shape memory region 100m2 having pores 100p2 (which are of a different size that than pores 100p1), disposed over a substrate 110 that contains multiple therapeutic-agent-filled depressions 120a, 120b, in accordance with an embodiment of the present invention. The depressions 120a, 120b may contain the same or differing therapeutic agents, they may be of the same or differing shapes, they may be of the same or differing sizes, and so forth.

Examples of techniques for forming depressions (e.g., blind holes, through holes, slots, trenches, etc.) for use in the invention include, for example, molding techniques, direct-write techniques, and mask-based techniques such as those described above.

"Therapeutic agents," "biologically active agents," "drugs," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention. Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o)agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.).

Specific examples of non-genetic therapeutic agents, not necessarily exclusive of those above, include paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including a-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and O-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (1) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 assigned to NeoRx Corporation, the entire disclosure of which is incorporated by reference.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising: (a) a porous region comprising pores having pore widths and (b) a therapeutic agent disposed within, beneath or both within and beneath said porous region, said porous region comprising a shape memory material capable of undergoing a change in configuration such that said pores undergo an increase or decrease in pore width upon subjecting said porous region to an activating stimulus.

2. The implantable or insertable medical device of claim 1, wherein said porous region is a metallic porous region.

3. The implantable or insertable medical device of claim 1, wherein said porous region comprises an alloy comprising nickel and titanium.

4. The implantable or insertable medical device of claim 1, wherein the increase or decrease in width comprises:
 (a) contraction of said pores; or
 (b) expansion of said pores upon being subjected to said activating stimulus.

5. The implantable or insertable medical device of claim 1, wherein said porous region is a polymeric region.

6. The implantable or insertable medical device of claim 1, wherein said porous region comprises a block copolymer or a covalently cross-linked polymer network.

7. The implantable or insertable medical device of claim 1, wherein said porous region comprises a polymer network comprising tert-butyl acrylate and epoxy.

8. The implantable or insertable medical device of claim 1, wherein said porous region is formed from a solid material.

9. The implantable or insertable medical device of claim 1, wherein said porous region is formed from particles.

10. The implantable or insertable medical device of claim 1, wherein said porous region is formed from fibers.

11. The implantable or insertable medical device of claim 1, wherein said porous region is a nanoporous region.

12. The implantable or insertable medical device of claim 1, wherein said porous region comprises parallel pores.

13. The implantable or insertable medical device of claim 1, wherein said porous region comprises interconnected pores.

14. The implantable or insertable medical device of claim 1, wherein said pores decrease in width upon being subjected to said stimulus.

15. The implantable or insertable medical device of claim 1, wherein said pores increase in width upon being subjected to said stimulus.

16. The implantable or insert able medical device of claim 1, wherein said stimulus is a change in temperature.

17. The implantable or insertable medical device of claim 1, wherein said stimulus is selected from heat, electric current, pH change, pressure change, light and combinations thereof 18. The implantable or insertable medical device of claim 1, wherein said porous region is disposed over a substrate.

19. The implantable or insertable medical device of claim 18, wherein said substrate comprises a plurality of therapeutic-agent-containing depressions.

20. The implantable or insertable medical device of claim 18, wherein said substrate is a metallic substrate.

21. The implantable or insertable medical device of claim 18, wherein said substrate is a polymeric substrate.

22. The implantable or insertable medical device of claim 18, wherein said substrate is a ceramic substrate.

23. The implantable or insertable medical device of claim 18, wherein said substrate is a metallic, ceramic or polymeric stent body.

24. The implantable or insertable medical device of claim 1, wherein said device is selected from catheters, guide wires, balloons, filters, stents, grafts, stent grafts, vascular access ports, embolization devices, myocardial plugs, patches, pacemakers, pacemaker leads, left ventricular assist devices, total artificial hearts, heart valves, vascular valves, anastomosis clips and rings, and tissue engineering scaffolds.

25. The implantable or insertable medical device of claim 1, wherein said medical device is adapted for implantation or insertion into the coronary vasculature, peripheral vascular system, esophagus, trachea, colon, biliary tract, urogenital system, or brain.

26. The implantable or insertable medical device of claim 1, wherein said therapeutic agent is retained within said device.

27. The implantable or insertable medical device of claim 1, wherein said therapeutic agent is released from said device.

28. The implantable or insertable medical device of claim 27, wherein the release is selected from zero-order release, first order release, second order release, step-wise release, burst release, and combinations thereof.

29. The implantable or insertable medical device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-$\beta$ elevating agents, and agents that interfere with endogenous vasoactive mechanisms.

30. The implantable or insertable medical device of claim 1, further comprising an additional therapeutic agent.

31. The implantable or insertable medical device of claim 1, wherein the therapeutic agent is an immobilized therapeutic agent which is (a) within a temporary, deformed porous region, (b) immobilized beneath the porous region, or (c) positioned in both (a) and (b).

32. The implantable or insertable medical device of claim 1 wherein the porous region returns to its original shape upon removal of the activating stimulus.

33. The implantable or insertable medical device of claim 32 wherein transport of a bodily species from a bodily environment surrounding the device or catalytic products of the bodily species is (a) increased to and from the device by enlargement of the pore widths in vivo or ex vivo; or (b) decreased by shrinkage of the pore widths in vivo or ex vivo.

34. The implantable or insertable medical device of claim 32 wherein transport of a bodily species from a bodily environment surrounding the device or catalytic products of the bodily species is (a) increased to and from the device by enlargement of the pore widths in vivo or ex vivo; or (b) decreased by shrinkage of the pore widths in vivo or ex vivo upon being subjected to said activating stimulus.

* * * * *

UNITED STATES PATENT AND TRADEMARK OFFICE
CERTIFICATE OF CORRECTION

| | | |
|---|---|---|
| PATENT NO. | : 7,666,179 B2 | Page 1 of 1 |
| APPLICATION NO. | : 11/545439 | |
| DATED | : February 23, 2010 | |
| INVENTOR(S) | : Barron Tenney, Michael N. Helmus and Yixin Xu | |

It is certified that error appears in the above-identified patent and that said Letters Patent is hereby corrected as shown below:

Specification, col. 7, line 33, after "of", change "form" to --from--

Specification, col. 8, line 30, after "change", change "onto" to --into--

Specification, col. 8, line 66, after "longer", add --be--

Specification, col. 9, line 41, after "available", add --in--

Specification, col. 18, line 35, after "including" change "a" to --α--

Specification, col. 18, line 60, change "O-cyclodextrin" to --β-cyclodextrin--

Claim 16, col. 20, line 36, after "or", change "insert able" to --insertable--

Signed and Sealed this

Fifteenth Day of June, 2010

David J. Kappos
*Director of the United States Patent and Trademark Office*